US008244064B2

(12) United States Patent
Boese et al.

(10) Patent No.: US 8,244,064 B2
(45) Date of Patent: Aug. 14, 2012

(54) METHOD FOR REGISTERING AND MERGING MEDICAL IMAGE DATA

(75) Inventors: Jan Boese, Eckental (DE); Benno Heigl, Coburg (DE); Norbert Rahn, Forchheim (DE)

(73) Assignee: Siemens Aktiengesellschaft, München (DE)

( * ) Notice: Subject to any disclaimer, the term of this patent is extended or adjusted under 35 U.S.C. 154(b) by 1045 days.

(21) Appl. No.: 11/043,464

(22) Filed: Jan. 26, 2005

(65) Prior Publication Data

US 2005/0245807 A1    Nov. 3, 2005

(30) Foreign Application Priority Data

Jan. 29, 2004 (DE) .......................... 10 2004 004 620

(51) Int. Cl.
G06K 9/32 (2006.01)
(52) U.S. Cl. .......................... 382/284; 382/128; 382/294
(58) Field of Classification Search .......... 382/128–132, 382/287, 293, 294–296; 378/162; 600/407, 600/473, 414, 426
See application file for complete search history.

(56) References Cited

U.S. PATENT DOCUMENTS

| | | | | |
|---|---|---|---|---|
| 5,772,594 A * | 6/1998 | Barrick | ........................ | 600/407 |
| 5,880,976 A * | 3/1999 | DiGioia, III et al. | ............. | 703/7 |
| 6,006,126 A * | 12/1999 | Cosman | ........................ | 600/426 |
| 6,167,296 A * | 12/2000 | Shahidi | ........................ | 600/427 |
| 6,423,009 B1 * | 7/2002 | Downey et al. | ................ | 600/461 |
| 6,628,977 B2 * | 9/2003 | Graumann et al. | ............ | 600/407 |
| 7,139,418 B2 * | 11/2006 | Abovitz et al. | ................ | 382/132 |
| 7,302,286 B2 * | 11/2007 | Camus et al. | ................. | 600/407 |
| 7,570,791 B2 * | 8/2009 | Frank et al. | .................... | 382/132 |
| 7,697,972 B2 * | 4/2010 | Verard et al. | ................... | 600/424 |
| 2003/0072416 A1 * | 4/2003 | Rasche et al. | ................. | 378/197 |
| 2003/0083562 A1 | 5/2003 | Bani-Hashemi et al. | | |

(Continued)

OTHER PUBLICATIONS

Tomazevic et al., 3-D/2-D Registration of CT and MR to X-Ray Images, Nov. 2003, IEEE Transactions on Medical Imaging, vol. 22, No. 11, pp. 1407-1416.*

(Continued)

*Primary Examiner* — Matthew Bella
*Assistant Examiner* — Dennis Rosario

(57) ABSTRACT

The present invention relates to a method for the registration and superimposition of image data when taking serial radiographs in medical imaging, wherein a plurality of image data sets for a region of a patient (17) that is being investigated are constructed at time intervals using an imaging system (1) and are referenced with a first image data set for the region that is being investigated that was constructed previously using said imaging system (1). In the above method, a location system (2) is used during the production of serial radiographs constantly, or at least at a respective proximity in time to the construction of individual data sets, to determine a current spatial position of the region being investigated in a reference system that is firmly connected to the imaging system (1), whereby in the construction of the first image data set, a first spatial position of the region that is being investigated is recorded. In the construction of some or all further image data sets, the respective current spatial position of the region that is being investigated is determined and an image content of each first image data set is geometrically adapted on the basis of the difference between the first and the current spatial position, such that compensation is made for a different spatial position of the region that is being investigated. The geometrically adapted first image data set or an image data set derived therefrom, or an image data set that is positionally connected thereto by registration is then displayed superimposed with the respective further image data set.

9 Claims, 2 Drawing Sheets

U.S. PATENT DOCUMENTS

2003/0191394 A1* 10/2003 Simon et al. ............... 600/473
2005/0085715 A1* 4/2005 Dukesherer et al. .......... 600/424

OTHER PUBLICATIONS

Gueziec et al., Exploiting 2-D to 3-D Intra-Operative Image Registration for Qualitative Evaluations and Post-Operative Simulations, 1999, Springer-Verlag Berlin Heidelberg, pp. 820-833.*

Graeme P. Penney, Philipp G. Batchelor, Derek L. G. Hill, David J. Hawkes, Juergen Weese, "Validation of a Two-to Three-Dimensional Registration Algorithm for Aligning Preoperative CT Image and Intraoperative Fluoroscopy Images", Medical Physics, Jun. 2001, pp. 1024-1032, vol. 28, No. 6.

J. Weese, T.M. Buzug, G.P. Penney, P. Desmedt, "2D/3D Registration and Motion Tracking for Surgical Interventions", Philips Journal of Research, 1998, pp. 299-316, vol. 51, No. 2.

* cited by examiner

METHOD FOR REGISTERING AND MERGING MEDICAL IMAGE DATA

CROSS REFERENCE TO RELATED APPLICATIONS

This application claims priority to the German application No. 10 2004 004 620.4, filed Jan. 29, 2004 which is incorporated by reference herein in its entirety.

FIELD OF INVENTION

The present invention relates to a method for the registration and superimposition of image data when taking serial radiographs in medical imaging, wherein a plurality of image data sets for a region of a patient that is being investigated are constructed at time intervals using an imaging system and are referenced with a first image data set of the region being investigated that was constructed previously using said imaging system, in particular for the radiographic monitoring of medical interventions. The invention also relates to an imaging system for carrying out said method.

BACKGROUND OF INVENTION

In countless medical interventions, an instrument, for instance a catheter, has to be guided accurately through a patient's body channels. Such interventions are thus required, for example, in neuroradiology for the diagnosis and treatment of vascular and other diseases in the head, neck and spine. In such cases, a catheter is guided through the peripheral artery to the blood vessel that is of interest.

SUMMARY OF INVENTION

Guiding the instrument accurately is a challenging task. It is indeed in neuroradiological interventions that the guidance of the catheter though the arterial system can be complicated considerably by the large number of ramifications and convoluted parts of arteries. To assist the physician, it is known for the intervention to be assisted by an imaging system, in particular by an imaging method that uses a mono- or biplanar X-ray system. In such a method, two-dimensional projection images of the region that is being investigated are continually supplied and displayed to the physician during the intervention via the imaging system. The aforementioned images allow the current position of the instrument to be detected. However, orientation within the patient's anatomy becomes more and more difficult because the image detection is two-dimensional.

That is why techniques are used wherein, before the beginning of the intervention, a three-dimensional image data set of the region that is being investigated is constructed within the same C-arm imaging system and simultaneously displayed together with the 2D images during the intervention. The display can be effected by superimposing the 3D image data set on the respective 2D image data set. In this case the 2D image constructed in real time is superimposed with the previously obtained rendered 3D image data set in order to obtain a so-called 3D road map. A different option is that of transferring the position of an interesting feature, the tip of the catheter, for example, from the 2D images into the 3D image data set or vice versa. This can be effected either manually or by marking the respective position in the two images or by automatic detection of the catheter tip in the image data. Such a technique is also known by the term "linked cursor" technique. In the present application, both techniques have been subsumed into the concept of 2D/3D image superimposition.

An essential prerequisite for 2D/3D image superimposition is that the geometrical relationship between the 2D and 3D image data sets that have been constructed must be known. Where the object being investigated is not moving, this can be achieved with a simple calibration process, using a calibration phantom, for example. If the patient moves between the construction of the 3D image data set and the subsequent drawing of a 2D image, the calibration is no longer valid. In the case of neuroradiological interventions, this can, for example, result in the position of the catheter being shown incorrectly in the 3D images. A movement by the patient would then require a new 3D image data set to be constructed. As a result of the fact that the dose of radiation that can be applied is limited, and that the amount of contrast agent that can be applied is limited, such recalibrations cannot be carried out frequently, however.

Until now the incidence of this problem was reduced by registration of the 2D/3D image data sets. In this registration, the 3D image data set is adapted to the respective current 2D data set using geometrical operations, in particular translations and rotations. This is achieved by using the information contained in both data sets. One option for registration consists in identifying characteristic structures that are visible in both data sets. The two data sets are then aligned by using these structures. The structures can be anatomical landmarks, for example blood vessels or bones, or artificial markers that are affixed to the patient during the 3D and 2D imaging. A further option for registration is the use of image-based methods that attempt to maximize the similarity between artificially calculated projections from the 3D image data set and the 2D image.

Examples of 2D/3D registration can be found, for example, in the publications by J. Weese et al., "2D/3D Registration and Motion Tracking for Surgical Interventions", Philips Journal of Research 51 (1998), 299-316, and by G. P. Penney et al., "Validation of a two- to three-dimensional registration algorithm for aligning preoperative CT images and intraoperative fluoroscopy images", Med. Phys. 28 (6), June 2001, 1024-1032.

Registration based on artificial markers has the disadvantage, however, that the positioning of the markers is difficult, time-consuming and sometimes possible only using an invasive route. Furthermore, the markers have to be identified in the images. This requires interacting regularly with the user. In the case of registration based on anatomical features, accuracy is limited since such landmarks are difficult to pinpoint exactly. Registration techniques that are based on image processing frequently require very high processing power and corresponding processing time. Furthermore, such methods are often numerically unstable and likewise require interaction with the user.

Document DE 100 51 370 A1 relates to a method for accurately positioning a patient in radiotherapy or radiosurgery. In this field a computer tomograph is used to establish a three-dimensional image data set for the region that is being investigated, on the basis of which data set subsequent radiation therapy, the irradiation of a tumor for example, is planned. The patient then has to be positioned as accurately as possible opposite the linear accelerator that is used for the radiation therapy in order to maintain irradiation in the planned position as accurately as possible. In said document, as accurate as possible positioning is achieved by having radiographic images from two different directions constructed in the linear accelerator, by means of which images the matching of a position or deviation in a position can be determined from a comparison with corresponding reconstructed (virtual) radiographic images from the previously created 3D image data set. The patient's position can then be adapted to compensate for this deviation in position by moving the treatment table. Pre-positioning of the patient is achieved in this case by means of a computer-controlled and camera-controlled navigation and tracking system with the aid of artificial markers on the patient.

DE 102 50 655 A1 also describes a patient positioning system used for the same purpose as in DE 100 51 370 A1. To solve the problem of positioning, DE 102 50 655 A1 uses a surface image generator on both the CT scanner and on the linear accelerator, the images therefrom being compared and used to position the patient exactly.

It is therefore an object of the invention to provide a method for the registration and superimposition of image data when taking serial radio graphs in medical imaging that allows accurate superimposition without time-consuming user interaction.

The object is achieved by the claims. Advantageous variants of the method and a corresponding imaging system constitute the subject matter of the dependent claims or can be seen from the following description and likewise from the embodiments.

In the present method for the registration and superimposition of image data when taking serial radiographs in medical imaging, wherein a plurality of image data sets for a region of a patient that is being investigated are constructed at time intervals using an imaging system and are referenced with a first image data set of the region being investigated that was constructed previously using said imaging system, a location system is used with which a current spatial position of the region being investigated is determined in a reference system that is firmly connected to the imaging system, said location system being used, constantly or at least at a respective proximity in time to the construction of individual image data sets during the production of serial radiographs. In the construction of the individual image data set, which is preferably a 3D image data set, a first spatial position of the region being investigated is fixed. Similarly, in the construction of some or all further image data sets, where said sets are predominantly 2D image data sets, the respective spatial positions of the region being investigated are likewise constructed. After each further image data set has been constructed, the image content of the first image data set is geometrically adapted, in particular rotated and/or moved, on the basis of the difference between the first and the current spatial position, such that it is possible to compensate for a different spatial position of the region that is being investigated. The first geometrically adapted data set that is obtained in this way or an image data set derived therefrom, for example a rendered data set or a set that is positionally connected thereto by registration, is then displayed to the user superimposed by or combined with the respective further image data set or the image data set derived from said image data set, which includes, for example only a few details. Here, 2D/3D image superimposition techniques as disclosed in the introductory part of the description can be used.

An image data set that is positionally connected to said first image data set by registration can, for example, be an image data set that was constructed in another modality. Thus when using an x-ray C-arm device here to construct the first and the further image data sets, an image data set constructed with a CT, MR or PET unit can be used, for example.

The present method allows the registration and superimposition of image data sets to be achieved reliably and in real time, independent of the image quality, when taking serial radiographs in medical imaging. The method is particularly suitable for 2D/3D image registration and superimposition, particularly in the area of road mapping during a medical intervention. Registration of so-called 4D data sets, that is, of data sets that also contain time data in addition to three-dimensional position data, with other data sets is likewise possible using the present method. Since the method dispenses with artificial or anatomical markers it does not require time-consuming user interaction during the patient's treatment. The only additional step involved optionally consists in installing the position sensor for the location system and likewise optionally in calibrating said location system on one occasion. The calibration is very simple, however, and can easily be combined with the calibration for the 3D data acquisition. The proposed method for registration of the image data using the location system does not require any time-consuming computing operations and can thus be easily carried out in real time.

A device with which the position and orientation (6 degrees of freedom altogether) of a position sensor can be measured in three dimensions is preferably used as a location system. Examples of such location systems are optoelectronic position sensors, for example, OPTTRAK 3020, Northern Digital, Waterloo, Canada, or electromagnetic location systems, such as, for example, Biosense Webster Inc., Diamond Bar, Calif., USA or the Bird System from the Ascension company in Milton, Vt., USA. Other location systems with which the spatial position of the region being investigated can be determined can also be used of course. Thus, it is possible, for example, to install 3 position sensors on the object under investigation, from the spatial position of which sensors it is possible to deduce the orientation of the region that is being investigated. Optical scanning systems or suchlike that function without a sensor being fitted to the patient are also possible.

The present imaging system comprises at least one x-ray source and a detector, a treatment table, a control unit, a registration unit, an image processing unit and an image display unit, said image processing unit for the superimposed display of a stored data image set being designed such that at least one image data set that has just been constructed is displayed on the image display unit. The imaging system is characterized by the fact that the registration unit and the image processing unit are designed for the registration and superimposition of images on the basis of current position data in a location system according to the aforementioned method. The registration unit in particular is designed such that it activates the image processing unit in real time for geometrical adaptation of an image content of the stored image data set on the basis of a patient's movement that has been detected by a location system, such that when the stored image data set is superimposed with the image data set that has just been constructed, compensation is made for the movement that has been detected.

BRIEF DESCRIPTION OF THE DRAWINGS

The present method and the device pertaining thereto will be explained again in more detail below by means of an embodiment and in connection with the drawings. The drawings show.

DETAILED DESCRIPTION OF INVENTION

The present method is hereafter described by means of an x-ray angiography unit for applications in neuroradiology. The method can of course be used in other areas of medical imaging in which serial radiographs are taken and sometimes have to be displayed superimposed with a previously constructed image data set.

Figure 1:
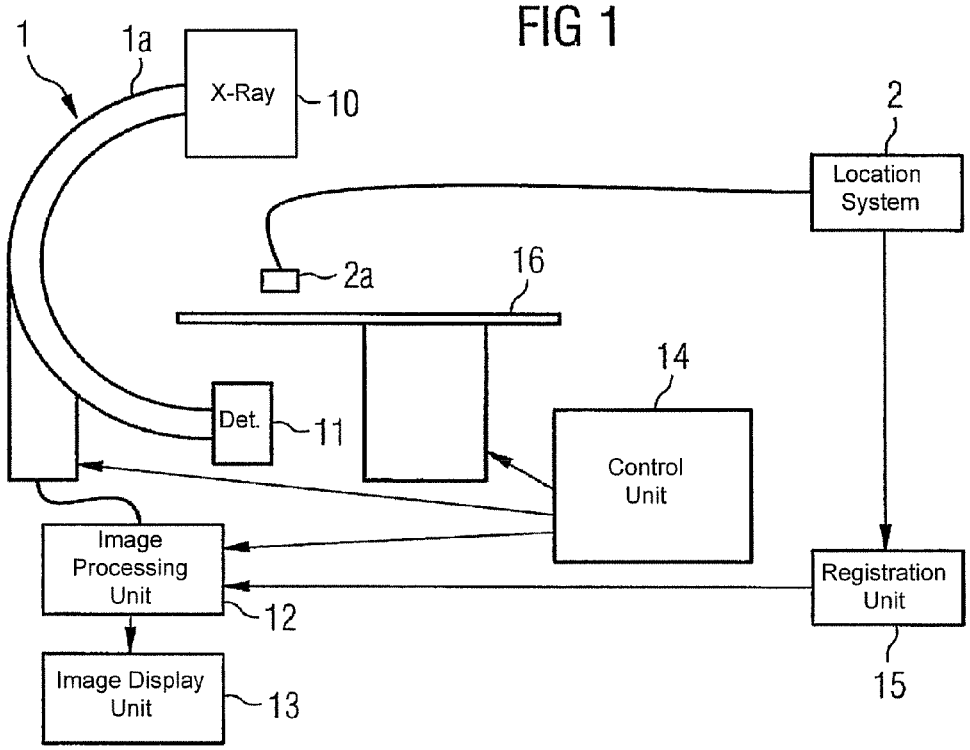
FIG. 1 an example of a C-arm device as an imaging system for carrying out the aforementioned method.

For the radiographs an x-ray angiography unit 1 for neuroradiology is used, as shown in diagram form in FIG. 1. The x-ray angiography unit 1 consists inter alia of a C-arm 1a that is rotatable round two axes, to which are attached an x-ray tube 10 and a detector 11 opposite said x-ray tube, an image processing unit 12 and an image display unit 13. Said unit furthermore comprises the treatment table 16, a control unit 14 to control the taking of the radiographs and the registration unit 15. By rotating the C-arm 1a, various projections of the region being investigated can be constructed as two-dimensional images during the examination of the patient who is lying on the treatment table 16. The x-ray angiography unit 1 that is shown also offers the option of taking rotation angiographs and 3D images. In the present method a location system 2 is used to determine the position of the region of the patient which is being investigated, which in the present example is the patient's head. In the present example, said location system 2 is a device with which the position and orientation of a position sensor 2a can be measured in three dimensions.

Figure 2:
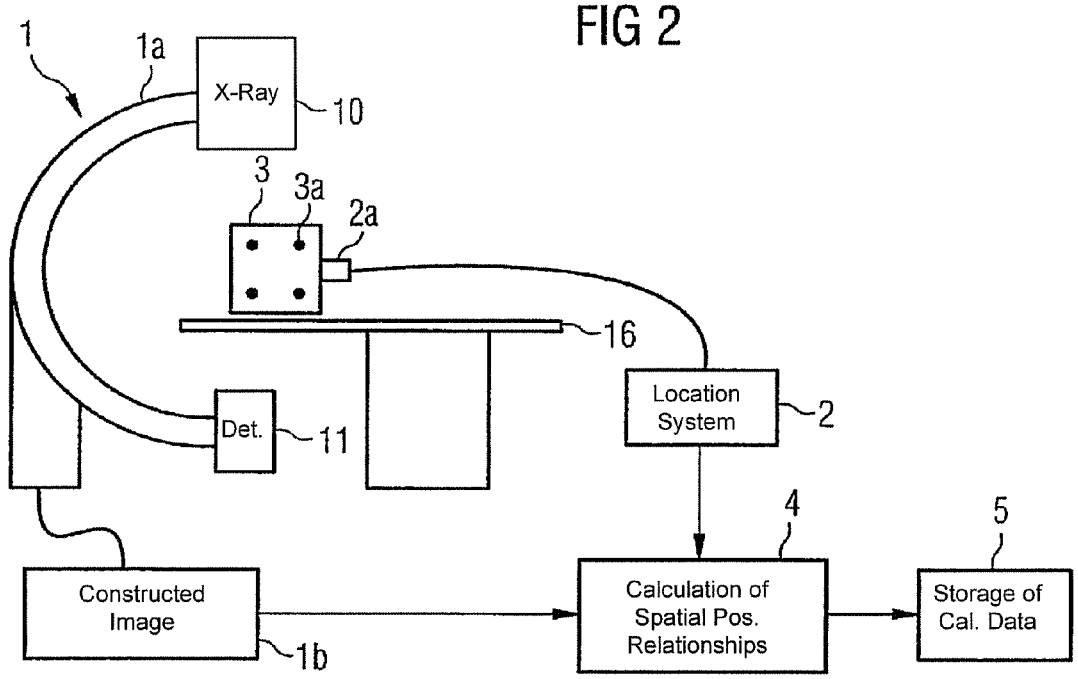
FIG. 2 an example of the calibration of the location system in the C-arm device shown in FIG. 1.

Before using the location system 2, a calibration has to be made between the systems of coordinates in the angiography unit 1 and of the location system 2. The calibration consists of 6 parameters that describe the rotation and translation of the two coordinate systems relative to each other. Various methods are available for carrying out such a calibration. They are:

One option for calibration consists in using a calibration phantom 3 that is constructed by means of x-ray imaging from various angles as illustrated in FIG. 2. During the construction of image 1b, the sensor 2a of the location system 2 is connected to the calibration phantom 3. As a result of the fixed relationship between the marks 3a on the phantom 3, which can be detected on the constructed x-ray images, and the sensor 2a, the spatial position of the sensor 2a (and consequently of the system of coordinates of the location system) can be calculated relative to the system of coordinates of the angiography unit 1 in a calculation step 4. Said relationships or calibration data are stored (5).

A further calibration technique relates to the calibration of an electromagnetic location system. Here the transmitter could be installed at a point, the position of which relative to the system of coordinates of the angiography unit is known. In this case no further steps are required for the calibration.

When an optical location system is used, a marker plate could be installed on the detector or on another part of the angiography unit, the position whereof relative to the system of coordinates of the angiography unit is known. Here, too, no further calibration steps are required. In this case a further option without any additional calibration steps consists in installing the camera of the optical location system such that it is fixed to the ceiling of the investigation room.

The calibration that is carried out in the present example using the first technique described is generally only required on one occasion when the system is installed.

Figure 3:
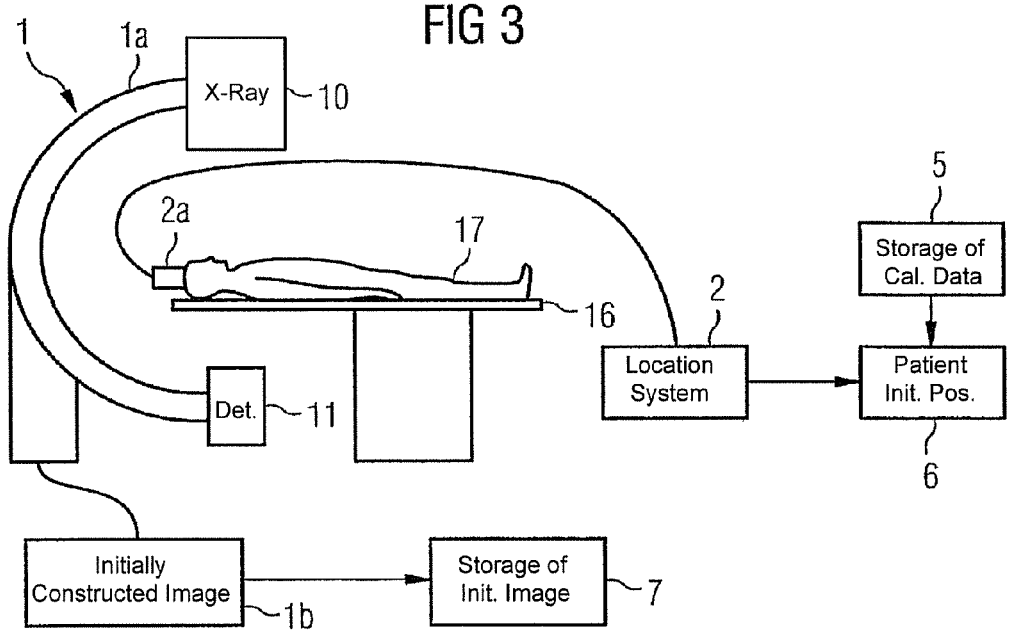
FIG. 3 an example of the construction of the first image data set having the first spatial position of the region that is being investigated.
Figure 4:
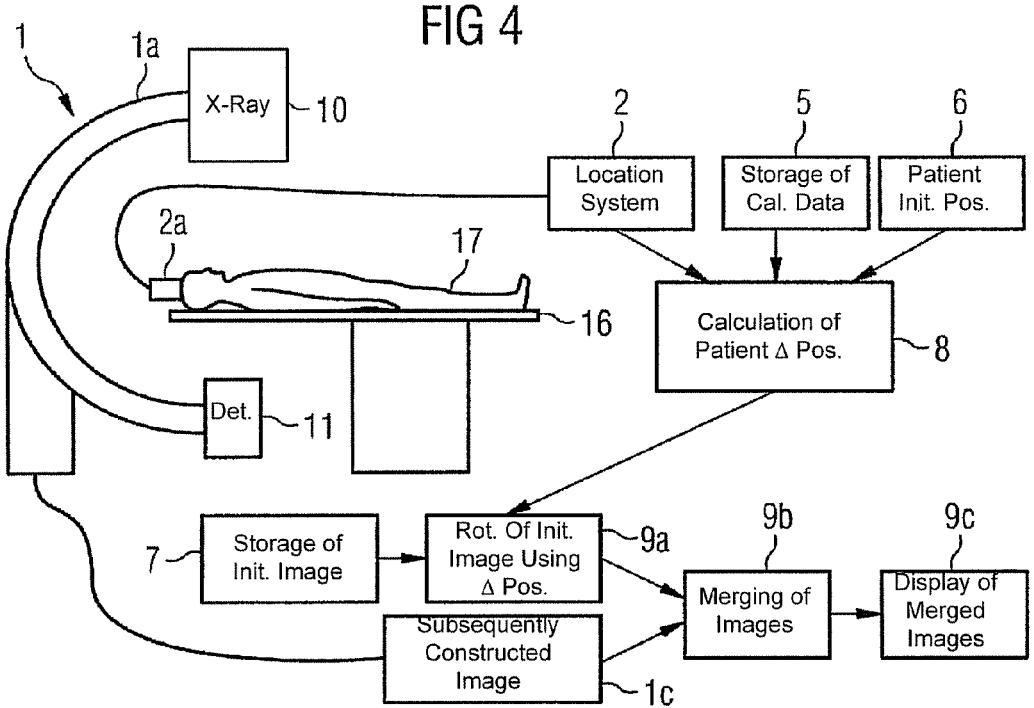
FIG. 4 an example of the construction of further image data sets and likewise of the superimposition thereof.

The procedure for carrying out the present method is shown in FIGS. 3 and 4. First the sensor 2a of the location system 2 is attached to the head of the patient 17, as shown by the diagram in FIG. 3. This can be achieved using an adhesive connection, for example. Directly before the construction 1b of a 3D image data set, the current position of the sensor 2a and thus of the head of the patient 17 is determined automatically by the location system 2, that is, without any user interaction. This initial position, that is the position and orientation, is calculated (block 6), taking into account the stored calibration data 5 in the reference system of the imaging system 1 and likewise stored. The 3D radiograph is then taken and the resulting 3D image data set is likewise stored (7).

During the taking of the subsequent images 1c of the 2D image data, the respective current position of the sensor 2a is constantly determined by the location system 2. By comparing the stored initial position and the current position of the sensor 2a, a patient's movement (Δ Pos (change in position) is calculated (block 8) in the registration unit 15 (FIG. 1) taking into account the calibration (cal.) data 5. Using this information, the stored 3D image data set is rotated and moved accordingly (9a). The respective constructed 2D images and the converted 3D image data set are then superimposed (9b) and the superimposed image is shown on an image display unit 13 (9c).

Furthermore, in addition to the conversions for a rigid body that have been considered hitherto, it is also possible to effect a registration with respect to elastic parts of the body, such as the thorax for example. A plurality of sensors can thus be installed on the thorax, which sensors determine the elastic movement. Using appropriate geometrical conversion of the first image data set, said movement can be registered and superimposed with the respective further image data sets.

The invention claimed is:

1. A method of registering and merging medical image data to guide an interventional instrument through a body channel of a patient, comprising:

recording an initial image data set of an examination area of the patient by an imaging system, wherein the initial image data set is a three-dimensional image data set;

using at least one external sensor in a location detecting system to determine a first spatial position of an external body part of the patient related to the examination area of the patient, wherein the first spatial position corresponds to the position of the examination area when the initial image data set is recorded by the imaging system;

recording a plurality of serial examination image data sets of the examination area at specified time intervals by the imaging system, wherein the serial examination image data sets are two-dimensional image data sets to monitor in real-time the interventional instrument being guided through the body channel of the patient;

determining with the location detecting system a current spatial position of the body part of the patient;

relating the current spatial position to a reference coordinate frame where coordinates are assigned by the location detecting system to the imaging system while recording in real-time with the imaging system a current serial examination image data set of the examination area, wherein the frame of reference assigned by the location detecting system to the imaging system is connected to the imaging system;

determining in a registration unit a spatial position difference between the first and the current spatial position, wherein said spatial position difference is determined in the frame of reference assigned by the location detecting system to the imaging system;

adapting the initial three-dimensional image data set using the determined difference such that the adapted initial three-dimensional image data set corresponds to the current spatial position without use of artificial markers or anatomical markers, wherein adapting the initial image three-dimensional data set using the determined spatial position difference includes a translation relative to the current serial examination two-dimensional image data set, said translation having three degrees of translation freedom, the adapting of the initial image data set further includes a rotation having three degrees of rotation freedom, thereby said adapting providing a total of six degrees of freedom; and merging and jointly displaying in an image display unit the adapted initial three dimensional image data set superimposed with respect to the current serial examination two dimensional image data set of the examination area recorded in real time to obtain a three-dimensional road map conducive to guide in real-time the interventional instrument through the body channel of the patient.

2. The method according to claim 1, wherein the current serial examination image data set includes a further image data set derived from the current serial examination image data set.

3. The method according to claim 1, wherein the current spatial position is determined continuously.

4. The method according to claim 1, wherein the current spatial position is determined substantially simultaneously with recording a serial examination image data set.

5. The method according to claim 1, wherein the imaging system comprises an x-ray C-arm device.

6. The method according to claim 1, wherein an image data set recorded by a further imaging system is registered with the initial image data set with regard to corresponding spatial positions present both in the initial image data set and the image data set recorded by a further imaging system, and the registered image data set and the current serial examination image data set are merged and jointly displayed.

7. The method according to claim 1, wherein the steps of adapting the initial image data set and merging and jointly displaying the adapted initial image data set and the current serial examination image data set are executed in real time.

8. An imaging system, comprising:
at least one radiation source;
a radiation detector;
a treatment table;
a control unit for controlling a recording of a plurality of radiographic medical images;
a location detecting system including at least one sensor to determine spatial positions of an external body part of a patient related to an examination area of the patient;
a registration unit for registering at least two medical images with each other with regard to corresponding spatial positions present in both medical images;
an image processing unit; and
an image display unit, wherein the registration unit and the image processing unit are arranged and configured to perform the following steps to guide an interventional instrument through a body channel of a patient:

recording an initial image data set of the examination area of the patient by the image processing unit, wherein the initial image data set comprises is a three-dimensional image data set;

configuring the location detecting system to determine a first spatial position of the body part of the patient, wherein the first spatial position corresponds to the position of the examination area when the initial image data set is recorded by the imaging system;

recording a plurality of serial examination image data sets of the examination area at specified time intervals by the image processing unit, wherein the serial examination image data sets are two-dimensional image data sets to monitor in real-time the interventional instrument being guided through the body channel of the patient;

determining with the location detecting system a current spatial position of the body part of the patient;

relating the current spatial position to a reference coordinate frame where coordinates are assigned by the location detecting system to the image processing unit while recording in real-time with the imaging system a current serial examination image data set of the examination area, wherein the frame of reference assigned by the location detecting system to the imaging system is connected to the imaging system;

determining a spatial position difference between the first and the current spatial position by the registration unit, wherein said spatial position difference is determined in the frame of reference assigned by the location detecting system to the imaging system;

adapting the initial three-dimensional image data set using the determined difference such that the adapted initial three-dimensional image data set corresponds to the current spatial position, by the registration unit without use of artificial markers or anatomical markers, wherein adapting the initial image three-dimensional data set using the determined spatial position difference includes a translation relative to the current serial examination two-dimensional image data set, said translation having three degrees of translation freedom, the adapting of the initial image data set further includes a rotation having three degrees of rotation freedom, thereby said adapting providing a total of six degrees of freedom; and merging and jointly displaying with the image display unit the adapted initial image data set superimposed with respect to the current serial examination image data set of the examination area recorded in real time with the imaging system to obtain a three-dimensional road map conducive to guide in real-time the interventional instrument through the body channel of the patient.

9. The imaging system according to claim 8, wherein the imaging system is an x-ray C-arm device.

* * * * *